US012805966B2

(12) United States Patent
Bäumer et al.

(10) Patent No.: US 12,805,966 B2
(45) Date of Patent: Nov. 24, 2026

(54) METHOD OF MEDICAL NAVIGATION

(71) Applicant: Carl Zeiss Meditec AG, Jena (DE)

(72) Inventors: Richard Bäumer, Schorndorf (DE); Matthias Karl, Königsbronn (DE)

(73) Assignee: Carl Zeiss Meditec AG, Jena (DE)

( * ) Notice: Subject to any disclaimer, the term of this patent is extended or adjusted under 35 U.S.C. 154(b) by 454 days.

(21) Appl. No.: 18/100,875

(22) Filed: Jan. 24, 2023

(65) Prior Publication Data

US 2023/0248467 A1 Aug. 10, 2023

(30) Foreign Application Priority Data

Feb. 4, 2022 (DE) ......................... 102022102698.1

(51) Int. Cl.
*A61B 90/00* (2016.01)
*A61B 34/20* (2016.01)
*G06T 7/80* (2017.01)

(52) U.S. Cl.
CPC .............. *A61B 90/36* (2016.02); *A61B 90/39* (2016.02); *G06T 7/80* (2017.01); *A61B 2034/2065* (2016.02); *G06T 2207/30204* (2013.01)

(58) Field of Classification Search
CPC . A61B 90/36; A61B 90/39; A61B 2034/2065; A61B 34/25; A61B 90/30; A61B 2090/371; A61B 2090/3983; A61B 90/20; A61B 2090/367; A61B 34/20; A61B 90/361; A61B 90/37; A61B 2034/2068; G06T 7/80; G06T 2207/30204;
(Continued)

(56) References Cited

U.S. PATENT DOCUMENTS

2006/0173356 A1* 8/2006 Feilkas .................... A61B 5/06
600/476
2017/0000581 A1* 1/2017 Tokuda .................. G06V 10/40
(Continued)

FOREIGN PATENT DOCUMENTS

WO WO-2016059250 A1 * 4/2016 ............ A61B 34/20

OTHER PUBLICATIONS

Office Action in Chinese Patent Application No. 202310085898.6 with English translation, dated Jun. 26, 2025, (25 pages).
(Continued)

*Primary Examiner* — Wassim Mahrouka
(74) *Attorney, Agent, or Firm* — NIXON PEABODY LLP; Jeffrey L. Costellia

(57) ABSTRACT

The present disclosure relates to a method of medical navigation including the method steps of: capturing a first image representation of a medical marker in a first perspective; capturing a second image representation of the medical marker in a second perspective; determining a three-dimensional representation of the medical marker on the basis of the first image representation and the second image representation; capturing a third image representation of the medical marker; and determining a spatial pose of the medical marker on the basis of a comparison of the third image representation and the three-dimensional representation of the medical marker. The present disclosure further relates to a medical navigation system, to a computer program and to the use of a three-dimensional representation of a medical marker for registering a medical instrument, a patient and/or a piece of medical equipment.

16 Claims, 3 Drawing Sheets

(58) Field of Classification Search
CPC ........... G06T 7/337; G06T 2207/10048; G06T 2207/10081; G06T 7/85; G06T 2207/10016; G06T 2207/10056; G06T 2207/30244; G06T 7/74; G06N 20/00; G16H 40/40
See application file for complete search history.

(56) References Cited

U.S. PATENT DOCUMENTS

| | | | | |
|---|---|---|---|---|
| 2018/0035966 | A1* | 2/2018 | Merlet | G06T 7/33 |
| 2019/0183583 | A1 | 6/2019 | Hong | |
| 2019/0328466 | A1* | 10/2019 | Schwägli | A61B 6/547 |
| 2020/0051280 | A1* | 2/2020 | Urban | G06T 7/50 |
| 2022/0039874 | A1* | 2/2022 | Choi | A61B 90/37 |
| 2022/0058829 | A1* | 2/2022 | Stopp | A61B 34/20 |

OTHER PUBLICATIONS

Feb. 4, 2022 German Office Action issued in German Application No. 10 2022 102 698.1. (12 pp.).

* cited by examiner

METHOD OF MEDICAL NAVIGATION

CROSS-REFERENCE TO RELATED APPLICATIONS

The present application claims priority under 35 U.S.C. § 119 to German Patent Application No. 102022102698.1, filed Feb. 4, 2022, the contents of which are incorporated by reference herein in their entirety.

SUBJECT MATTER OF THE INVENTION

The present invention relates to a method of medical navigation and a medical navigation system, in particular using a medical marker. The present invention further relates to a computer program for carrying out the method according to the invention in the system according to the invention, and to the use of a three-dimensional representation of a medical marker for registering a patient, a piece of medical equipment and/or a medical instrument.

Technological Background

The use of technological aids is part and parcel of modern medicine. Imaging methods and robotic systems for guiding medical instruments are used equally as a matter of course in both surgery and diagnostics. In this context, the use of imaging methods allows the discrimination of various structures in the patient and the image data obtained in the process can be used advantageously in diagnostics, and also in therapeutic and surgical methods.

By way of example, not only do 3-D image data of a patient allow a surgeon to plan a surgical intervention better, but the said 3-D image data can also assist the implementation of the said intervention. In particular, image information obtained during the operation can be overlaid on diagnostic 3-D image data obtained in advance in order to indicate poorly visible tissue boundaries to the surgeon. Likewise, robotic surgical instruments can be controlled or perform certain operations in partly or fully automated fashion on the basis of the 3-D image data.

In this context, correct linking of 3-D image data to a reference coordinate system is of essential importance to the aforementioned applications. In this case, the reference coordinate system can be the coordinate system of the patient during an intervention, the coordinate system of image information captured during the intervention or the coordinate system of the robotic system of a surgical microscope. Only such linking allows subsequent error-free medical navigation of the surgeon on the basis of the image data or of the robotic aids by means of the image data.

Linking 3-D image data to a certain reference coordinate system for the purposes of medical navigation is usually referred to as a "registration". Such a registration allows unique mapping of coordinates of the patient space to corresponding coordinates of the image space. Once such a mapping is known, structures of the patient situated at defined coordinates of the patient space can be represented at the corresponding coordinates in the image space, for example overlaid on 3-D image data determined presurgery. Moreover, poses (position and orientation) and movements of instruments and probes relative to the patient in the patient space and relative to the images in the image space are controllable.

As a rule, such a registration is carried out using medical markers which allow the spatial positions of the said markers, or of objects equipped therewith, to be determined in a coordinate system. To this end, the geometry of the markers is predetermined and moreover able to be captured by means of imaging methods. Hence, by evaluating one or more images of such a marker, it is possible to determine the pose (position and orientation) thereof in the coordinate system. When one camera is used, at least three marker elements, the relative spatial pose of which with respect to one another is known, are generally captured in order to determine the pose of a marker.

If, further, the relative spatial pose of the marker with respect to an object is known, the spatial pose of the object can also be determined in the coordinate system. The object can be a surgical instrument, a probe, a patient couch or parts of the patient themselves. If the data relating to the spatial pose of the object are made available to a medical navigation system, the latter can process the tracking data of the object together with other data determined in the coordinate system or registered therewith. By way of example, this allows the virtual representation of a medical instrument in a correct spatial relationship with respect to an anatomical structure and the implementation of a surgical intervention on the patient with the aid of image guidance.

Markers used for such a registration frequently have a rigid arrangement of at least three marker elements. Such marker elements can be printed onto the marker in planar fashion or have an elevated embodiment, and should be uniquely identifiable. In this case, the marker elements can be arranged in planar fashion or in different planes.

An exemplary marker according to the prior art is depicted in attached FIG. 5. A method for calibrating objects in a reference coordinate system is described in DE 102018119343 A1. Fastening a marker to a medical instrument is known from DE 202015106804 U1, and WO 2016/059250 A1 discloses the use of a marker for medical instrument navigation.

The accuracy of the medical registration is decisively determined by the accuracy with which the marker pose is determined. The latter is disadvantageously limited by tolerances in the production methods and of the fastening means of the markers. Even small deviations in the geometry have large effects on the determined pose of the marker, especially if the imaging sensors used for the registration are far away from the marker. Moreover, even small changes in the pose of a registered object relative to a marker fastened thereto can lead to an incorrect medical navigation, especially in the case of surgical microscopes which have a large working distance between marker and imaging sensor.

The object of the present invention is to overcome the disadvantages of the prior art and to provide an improved medical navigation.

DESCRIPTION OF THE INVENTION

The object according to the invention is achieved by the subjects of the independent patent claims. Preferred developments are the subject matter of the dependent claims.

A first aspect of the present disclosure relates to a method of medical navigation. Medical navigation is preferably the navigation of the surgeon on the basis of superposed image data or the navigation of robotic aids on the basis of image data of the patient. In a first step of the method according to the invention, a first image representation of a medical marker is captured in (from) a first perspective. The medical marker is preferably a medical marker having a plurality of marker elements that are distinguishable from one another, that is to say that are individually detectable, for example in accordance with attached FIG. 5. Preferably, at least some of the marker elements, preferably all marker elements, are uniquely distinguishable from one another. Within the scope of the present disclosure, a perspective preferably denotes the relative standpoint, in relation to the marker, from which the image representation of the marker is captured. Within the scope of the present disclosure, the term target may be used synonymously to replace the term marker, with in this case the term marker being able to be used synonymously to replace the term marker element. According to this alternative designation, the target has a plurality of individually detectable (distinguishable) markers. Preferably, at least some of the markers of the target, preferably all markers, are uniquely distinguishable from one another.

In a further step of the method according to the invention, a second image representation of the medical marker is captured in (from) a second perspective. Capturing the medical marker from a second perspective advantageously allows the derivation of depth information of the geometry of the marker on the basis of two-dimensional image representations, or the derivation of highly accurate depth information on the basis of three-dimensional image representations. As a matter of principle, both two-dimensional and three-dimensional image representations of the marker can be used within the scope of the method according to the invention. The first and/or second image representation of the medical marker can preferably consist only of the image representations of the marker elements of the medical marker, for example when capturing the first and/or second image representation under illumination with IR light and IR reflective marker elements. Likewise preferably, the first and/or second image representation may however also image the specific spatial shape of the marker, for example when capturing the image representations under illumination with visible light.

In a further step of the method according to the invention, a three-dimensional representation of the medical marker is determined on the basis of the first image representation and the second image representation. It is necessary to use at least two image representations in order to derive depth information from two-dimensional image representations. In the method according to the invention, preferably a plurality, particularly preferably a multiplicity, of image representations of the marker, captured from different perspectives in each case, are used to determine the three-dimensional representation. Within the scope of the present disclosure, the three-dimensional representation of the marker preferably denotes a three-dimensional model of the shape or geometry of the marker. Particularly preferably, the three-dimensional representation of the marker comprises the geometry of the marker elements and their relative spatial pose with respect to one another. Moreover, knowledge of the specific spatial shape of the marker is not necessary, but not damaging either. The determination of a three-dimensional representation of a real object on the basis of two-dimensional or three-dimensional image representations by means of photometric methods is known to a person skilled in the art from the prior art. To this end, many different software solutions are commercially available, and so it is possible to dispense with a detailed description of the 3-D representation of the marker. Preferably, the three-dimensional representation of the medical marker is determined with computer assistance in the method according to the invention, particularly preferably using machine learning (AI) algorithms. The three-dimensional representation of the marker is consequently particularly preferably available on a data medium as a computer-readable model of the medical marker.

In a further step of the method according to the invention, a third image representation of the medical marker is captured. In this case, the third image representation is preferably of the same type as the first and/or the second image representation of the medical marker. Further preferably, the third image representation of the medical marker is captured from a third perspective. If preferably a plurality, particularly preferably a multiplicity, of image representations of the marker, captured from different perspectives in each case, are used in the method according to the invention for determining the three-dimensional representation, the third image representation is preferably one of this plurality, particularly preferably multiplicity, of image representations.

A spatial pose of the medical marker is determined in a further step of the method according to the invention on the basis of a comparison of the third image representation of the medical marker and the three-dimensional representation of the medical marker. Expressed differently, according to the invention, the third image representation of the medical marker serves the registration of the medical marker as explained at the outset. In contrast to the prior art, however, a representation of the geometry (spatial shape) of the marker is not predetermined, but is determined as a three-dimensional representation in the process according to the invention itself. This geometry is compared with the third image and the pose of the marker is determined on the basis of this comparison.

For example, a pose determination of the marker is performed based on a comparison of the previously determined three-dimensional representation and the third image by means of a pose estimation algorithm (for example "perspective-n-point"). Exemplarily, such an algorithm solves an optimization problem by comparing different three-dimensional projections of the medical marker with the third image of the marker. Therein, each projection is based on the three-dimensional representation of the marker and a particular assumed pose of the marker (position and orientation), respectively. The algorithm then determines the projection that has the smallest deviation from the third image of the marker. The pose associated with this projection is then determined as the actual pose of the marker.

If the marker preferably comprises a plurality of distinguishable and individually detectable marker elements, then the three-dimensional representation preferably contains information on the spatial relationships (position and relative arrangement), sizes and/or shapes of the marker elements. The comparison of the third image of the medical marker and the three-dimensional representation of the medical marker then preferably comprises a comparison of the spatial relationships, sizes and/or shapes of the marker elements in the third image with the spatial relationships, sizes and/or shapes of the marker elements in the three-dimensional representation. Also here the comparison can be made by an algorithm for pose estimation and projections of the marker can be determined on the basis of the three-dimensional representation and assumed poses of the marker, and the pose of that projection with the smallest deviation from the third image of the marker can be determined as the actual pose of the marker.

In this case, the determination of the spatial pose of the medical marker, that is to say the registration, is carried out with reference to a reference coordinate system, for example the coordinate system of a patient during an operation, the coordinate system of a surgical microscope and/or the coordinate system of presurgical image data. The spatial pose preferably comprises the pose of the marker, that is to say position and orientation.

The method according to the invention advantageously allows a registration of the marker for medical navigation with improved accuracy and is further advantageously largely invariant in relation to variations in the geometry of the medical marker that are due to production or caused by wear or incorrect handling. Moreover, it is easily possible to integrate the method according to the invention in existing methods for registering medical markers. By way of example, the image representations can advantageously be captured in the same piece of equipment, for example a surgical microscope, as is used for the subsequent registration of the medical marker. Further advantageously, imaging properties of the piece of equipment used for registration are considered at least intrinsically in the method according to the invention.

In a preferred implementation of the method according to the invention, the first image representation, the second image representation and/or the third image representation are determined by means of at least one imaging method. Preferably, the same or similar imaging methods are used for all image representations; the same or similar imaging methods are particularly preferably used at least for the first and second image representation, or for the image representations used to create the three-dimensional representation. Preferably, the image representations are captured by means of at least one camera, with a spectral range captured by the image sensor of the camera preferably being dependent upon the utilized illumination source. By way of example, visible light and/or infrared light is used for illumination purposes in a surgical microscope and this is captured by at least one image sensor of a camera. Likewise preferably, x-ray radiation is used for illumination purposes in a computed tomography device and this is captured by at least one sensor of an x-ray detector. Likewise preferably, laser scanning is used to capture the first, second and/or third image representation of the medical marker. Advantageously, the method according to the invention is realizable using a multiplicity of imaging methods and consequently applicable in very different pieces of medical equipment. Further, the same or different (intrinsically and extrinsically calibrated) imaging methods can be used within the scope of the method according to the invention for the purposes of capturing the imaging representations, as a result of which the method according to the invention further is advantageously versatility usable and portable.

The medical marker preferably has a predetermined (nominal) geometry. As a rule, medical markers with a predefined geometry are produced as exactly as possible. Further, the geometry is advantageously optimized in respect of capturing a spatial pose of the marker on the basis of two-dimensional image representations and to this end has, for example, marker elements arranged in different planes and having exactly predetermined absolute dimensions and relative spatial poses. In the method according to the invention, the three-dimensional representation of the medical marker is preferably determined on the basis of the first image representation, the second image representation and information relating to the predetermined (nominal) geometry of the marker. According to this implementation, the geometry of the three-dimensional representation is consequently not constructed purely on the basis of the captured image representations, but information relating to the target geometry of the marker is additionally taken into account. The method according to the invention in this implementation consequently differs from known methods in terms of the adjustment of the information relating to the predetermined (nominal) geometry on the basis of the captured image representations. Advantageously, this takes account of production-related variations and deviations in the geometry on account of ageing or for other reasons. According to this implementation, a three-dimensional representation of the medical marker is preferably already available, in particular as a computer-readable data set of a model, before the method according to the invention starts. According to the invention, this data set is adjusted on the basis of the at least two captured image representations.

In the method according to the invention, a relationship is determined between a coordinate system, $K_{A1}$, of the first image representation and a coordinate system, $K_{A2}$, of the second image representation, preferably by way of a parameter set of a rigid body transformation. As already explained above, the object of the method according to the invention lies in the determination of a spatial pose of the medical marker in a reference coordinate system. This reference coordinate system can be different from or identical to one of the coordinate systems $K_{A1}$ and $K_{A2}$. If the reference coordinate system differs from the coordinate systems $K_{A1}$ and $K_{A2}$, a relationship between one of the coordinate systems $K_{A1}$ and $K_{A2}$ and the reference coordinate system is preferably likewise determined by a parameter set of a rigid body transformation. In this case, a parameter set of a rigid body transformation preferably comprises three values for the rotation about the x-axis, the y-axis and the z-axis and also three values for the translation along the x-axis, the y-axis and the z-axis, that is to say a total of six parameters.

In particular, should the coordinate systems $K_{A1}$ and $K_{A2}$ correspond to at least one coordinate system of at least one imaging sensor, a parameter set of one rigid body transformation is sufficient to map points in one of the coordinate systems $K_{A1}$ and $K_{A2}$ onto points in the other one of the coordinate systems $K_{A1}$ and $K_{A2}$. Otherwise, a relationship between a coordinate system, $K_{A1}$ of the first image representation and a coordinate system of an associated imaging sensor is preferably determined by a set of intrinsic parameters. Likewise preferably, a relationship between a coordinate system, $K_{A2}$, of the second image representation and a coordinate system of an associated imaging sensor is determined by a set of intrinsic parameters. In this case, the intrinsic parameters determine a relationship between the coordinate system of the image representation and the coordinate system of the associated imaging sensor. In this case, the type of the intrinsic parameters depends, in particular, on the type of imaging sensor utilized, with imaging sensor in this case denoting both the actual sensor and the utilized optics. If intrinsic parameters should be taken into account, a relationship between a coordinate system of the first imaging sensor and a coordinate system of the second imaging sensor is preferably determined by a parameter set of a rigid body transformation.

In a further preferred implementation, the determination of the three-dimensional representation of the medical marker comprises further a transformation of the first image representation of the marker into the coordinate system, $K_{A2}$, of the second image representation using the parameter set, further preferably using intrinsic parameters and the parameter set. By way of example, the positions, shapes and/or sizes of marker elements and/or characteristic points of the marker in the coordinate system of the first image representation are transferred by calculation into positions, shapes and/or sizes of the marker elements and/or of the characteristic points of the marker in the coordinate system of the second image representation. Subsequently, a first deviation is determined between the transformed first image representation of the marker and the second image representation of the marker. Expressed differently, first deviations between the transformed positions, shapes and/or sizes of the first image representation and the corresponding positions, shapes and/or sizes of the second image representation are determined in the coordinate system of the second image representation. By way of example, the centre and radius of a circular marker element in the first image representation are transformed by calculation into the coordinate system of the second image representation and first deviations from the centre and radius of the corresponding marker element in the second image representation are subsequently determined in the coordinate system of the second image representation. According to this implementation, the three-dimensional representation of the medical marker is finally determined on the basis of the determined first deviation.

As an alternative and/or in addition, the determination of the three-dimensional representation of the medical marker comprises further a transformation of the second image representation of the marker into the coordinate system, $K_{A1}$ of the first image representation using the parameter set, further preferably using intrinsic parameters and the parameter set. By way of example, the positions, shapes and/or sizes of marker elements and/or characteristic points of the marker in the coordinate system of the second image representation are transferred by calculation into positions, shapes and/or sizes of the marker elements and/or of the characteristic points of the marker in the coordinate system of the first image representation. Subsequently, a second deviation is determined between the transformed second image representation of the marker and the first image representation of the marker. Expressed differently, second deviations between the transformed positions, shapes and/or sizes of the second image representation and the corresponding positions, shapes and/or sizes of the first image representation are determined in the coordinate system of the first image representation. By way of example, the centre and radius of a circular marker element in the second image representation are transformed by calculation into the coordinate system of the first image representation and second deviations from the centre and radius of the corresponding marker element in the first image representation are subsequently determined in the coordinate system of the first image representation. Further preferably, the three-dimensional representation of the medical marker is finally determined on the basis of the determined second deviation.

The aforementioned implementations advantageously allow an optimization of a three-dimensional representation of the medical marker by minimizing the determined first and/or second deviations. Provided the three-dimensional representation maps the geometry of the medical marker and the utilized imaging sensors are each calibrated intrinsically and extrinsically, the captured image representations can be converted into one another by calculation on the basis of parameter sets (of a rigid body transformation and/or determined on the basis of the extrinsic and intrinsic calibration parameters) and the corresponding optimization target has been achieved. Particularly preferably, the determination of the three-dimensional representation of the marker comprises the adjustment of the information relating to the predetermined geometry of the marker or of the 3-D model of the predetermined geometry of the marker on the basis of the determined first and/or second deviation, with the goal of minimizing these deviations.

Especially if more than two captured image representations are used, the method according to the invention can moreover be used to optimize the utilized parameter sets. To this end, the three-dimensional representation of the medical marker is not varied and there is, instead, a variation of the parameter sets for minimizing the determined first and/or second deviations. Particularly preferably, the optimization of the three-dimensional representation of the medical marker and the optimization of the utilized parameter sets are carried out alternately and/or using different image representations of the marker.

In a particularly preferred implementation of the method according to the invention, the first image representation of the medical marker is captured by a first camera and the second image representation of the medical marker is captured by a second camera. Expressed differently, two different cameras are used in the method according to the invention. Preferably, at least one camera, particularly preferably both cameras, is/are a camera of a surgical microscope. By way of example, the first camera is a main observer camera and the second camera is a surround camera of the same surgical microscope. Further preferably, at least one or each of the two cameras can be used to capture a plurality or multiplicity of image representations of the medical marker. In a likewise preferred implementation, the main observer camera captures the first image representation of the medical marker in the visible light range and the surround camera captures the second image representation of the medical marker in the infrared light range.

In the aforementioned preferred implementation, a relationship is defined between a coordinate system, $K_{K1}$, of the first camera and a coordinate system, $K_{A1}$, of the first image representation, preferably by way of first intrinsic parameters of the first camera. The first intrinsic parameters particularly preferably comprise a first effective focal length, the coordinates of a principal image point (centre of the distortion) of the first image representation, a first scaling factor and/or a first radial lens error coefficient (distortion coefficient). Likewise preferably, the second intrinsic parameters of the second camera preferably comprise a second effective focal length, the coordinates of a principal image point (centre of the distortion) of the second image representation, a second scaling factor and/or a second radial lens error coefficient (distortion coefficient). As an alternative to the aforementioned intrinsic parameters of Tsai's camera calibration, other intrinsic parameters can also be used, for example for Zhang's camera calibration (cf., for example, "A practical comparison between Zhang's and Tsai's calibration approaches", Li et al., Proceedings of the 29th International Conference on Image and Vision Computing New Zealand, November 2014 Pages 166-171, DOI: 10.1145/2683405.2683443).

In the aforementioned preferred implementation, a relationship is further preferably determinable between the coordinate system of the first camera, $K_{K1}$, and the coordinate system of the second camera, $K_{K2}$, on the basis of first and second extrinsic parameters. In this case, the first extrinsic parameters preferably define a relationship between the coordinate system $K_{K1}$ and a reference coordinate system and the second extrinsic parameters preferably define a relationship between the coordinate system $K_{K2}$ and the reference coordinate system. Expressed differently, the extrinsic parameters describe the external orientation of the respective camera, that is to say the position and alignment of the respective camera in the reference coordinate system. According to this implementation, a parameter set, which defines the relationship between the coordinate system of the first image representation, $K_{A1}$, and the coordinate system of the second image representation, $K_{A2}$, is preferably determinable on the basis of the first and second intrinsic parameters and the first and second extrinsic parameters. Such a parameter set preferably contains the first and second intrinsic parameters and a parameter set of a rigid body transformation determined on the basis of the first and second extrinsic parameters.

In a further preferred implementation of the method according to the invention, the first image representation is captured in a first position of a camera and the second image representation is captured in a second position of the same camera. Particularly preferably, the camera in this case is moved from the first position to the second position by way of a known kinematic system. The known kinematic system permits precise specifications in relation to the rotation of the camera about the x-axis, the y-axis and the z-axis and in relation to the translation of the camera along the aforementioned axes. Consequently, the method according to the invention is advantageously implementable using only a single camera. Further preferably, this implementation is also implementable with each camera of the above-described implementation, that is to say with the first and the second camera. The at least one camera is preferably a camera of a surgical microscope, for example a main observer camera or a surround camera. Within the scope of the present disclosure, a known kinematic system is understood to mean a kinematic system that enables a well-defined translation and/or rotation. The geometry of a kinematic system, in particular, must be sufficiently accurate for such a well-defined translation and/or rotation of the kinematic system. This is preferably achieved by high manufacturing quality and/or by a calibration.

In a likewise preferred implementation, the first image representation of a first pose of the medical marker is captured by a camera. Expressed differently, an image representation of the marker with the marker in a first position and orientation is captured. The second image representation of a second pose of the medical marker is then captured by the same camera. Particularly preferably, the marker in this case is moved from the first pose to the second pose by way of a known kinematic system. The known kinematic system permits precise specifications in relation to the rotation of the marker about the x-axis, the y-axis and the z-axis and in relation to the translation of the marker along the aforementioned axes. Consequently, the method according to the invention is advantageously implementable using only a single camera. Further preferably, this implementation is also implementable with each camera of the above-described implementation, that is to say with the first and the second camera. Likewise preferably, this implementation is also combinable with a movement of the camera, as described above, for example in order to capture image representations of each pose of the marker from different viewing angles (perspectives) by means of the same camera. The at least one camera is preferably a camera of a surgical microscope, for example a main observer camera or a surround camera.

In a further particularly preferred implementation of the method according to the invention, the medical marker is fastened to a medical instrument. The medical instrument is for example a medical probe, a pointer, an awl or the like. Preferably, the medical marker and the medical instrument are securely connected to one another or securely connectable to one another, for example by means of a non-detachable connection, an integral connection, a detachable connection, a cohesive connection, a force-fit connection and/or an interlocking connection.

According to this preferred implementation, the third image representation of the combination of the medical marker and the medical instrument is captured. Thereupon, a spatial pose (pose) of the combination of medical marker and medical instrument is determined on the basis of the captured third image representation and the created three-dimensional representation of the medical marker. Determining this pose preferably further comprises the determination of a first pose of the medical marker and, on basis of the determined first pose, the determination of a second pose of the medical instrument, in particular of a characteristic point on the medical instrument. In this case, the second pose is preferably determined by calculation, for example on the basis of a predetermined spatial pose relationship between medical marker and instrument, which is realized by the connection between medical marker and instrument. According to the present disclosure, in particular according to this implementation, one of the first and second image representations used to create the three-dimensional representation can also be used as the third image representation, that is to say to determine the spatial pose. Expressed differently, capturing two different image representations is sufficient in principle. However, as a rule, a multiplicity of image representations will already be used in practice to create the three-dimensional representation. In this case, the spatial pose of the medical marker can then be deduced for each of these captured image representations, that is to say the third image representation particularly preferably is one of the multiplicity of image representations. Likewise preferably, the first image representation, the second image representation and the third image representation differ from one another.

Such a transformation is described, for example, in DE 102018119343 A1. In this case, measurement points on a combination of medical marker and instrument are initially used to determine a target point of this combination, the target point having a fixed spatial relationship with respect to the captured measurement points. A tracking point of the combination, for example the tip of a pointer as medical instrument, is initially calibrated by virtue of this tracking point being positioned at a predefined calibration point that is able to be sensed by a sensor. A transformation between the target point and the tracking point, and consequently between the measurement points and the tracking point, is determined by means of the initial calibration. On the basis of this transformation, the position of the tracking point is subsequently determinable on the basis of the position of the measurement points as determined by a capturing apparatus.

The method according to the invention advantageously allows a more accurate implementation of the method described in DE 102018119343 A1 since the position of the at least three measurement points on a marker is determinable with increased accuracy on the basis of the three-dimensional representation of same created according to the invention. Moreover, the method according to the invention is however also able to be combined with other methods for determining the position of such a tracking point, in particular with methods for directly capturing such a tracking point by means of image recognition. By way of example, the method according to the invention is used to determine the pose of the marker in a plurality of image representations of a combination of medical marker and medical instrument. Moreover, for each image representation, a first position of the tracking point is determined by means of image recognition (optionally using AI) and a second position of the tracking point is determined by calculation on the basis of the determined pose of the marker and a predefined spatial pose relationship between marker and tracking point. On the basis of the difference of the first and second positions of the tracking point determined in this way for each image representation, it is possible to continually optimize the spatial pose relationship between marker and tracking point, for example by minimizing the said difference. Once the optimization has been completed, the tracking point can be determined with great accuracy on the basis of the marker pose without requiring a computationally complex image recognition of the tracking point (pointer tip, etc.). Advantageously, the transformations between the image representations need not be known to this end, that is to say the said combination can be moved manually for example between the image representations.

In a further preferred implementation of the method according to the invention, the first image representation and the second image representation of the combination of the medical marker and the medical instrument are further also captured and the three-dimensional representation of the combination of the medical marker and the medical instrument is determined on the basis of the first and second image representation. Expressed differently, the combination of medical instrument and medical marker is defined as a new marker in accordance with this implementation. According to this implementation, the spatial pose of the combination of medical marker and medical instrument is ultimately determined, advantageously directly, on the basis of the comparison between three-dimensional representation and third image representation. According to this preferred implementation, the first image representation, the second image representation, the third image representation, the three-dimensional representation and the spatial pose are determined for the combination of medical marker and medical instrument in each case. Expressed differently, the combination of medical marker and medical instrument is used for registration purposes in accordance with this implementation. This advantageously allows the definition of this combination as a marker in the method according to the invention, which as a result is adaptable to various applications and, additionally, uses the geometry of the medical instrument for the above-described optimization tasks, and thus increases the variability thereof.

In a further preferred implementation of the method according to the invention, there further is continuous monitoring of the three-dimensional representation of the marker. In this case, the third image representation, preferably a multiplicity of (third) image representations captured during the medical navigation, is used not only to capture the spatial pose but also to continuously optimize the three-dimensional representation of the medical marker. The aforementioned predefined spatial pose relationship between marker and tracking point, which can be used to determine the spatial pose (pose) of the tracking point (the tip, for example), is preferably monitored, that is to say regularly optimized, within the scope of the method according to the invention.

In a particularly preferred implementation, the medical marker and the medical instrument are detachably connected to one another, for example by means of a plug-in connection, a clipping connection, a latching connection, a bayonet connection and/or a clamping connection. If, however, the combination of medical marker and medical instrument is used for registration purposes, it is possible to take into account possible variations in the relative pose between medical marker and instrument during various registrations. By way of example, a registration of the combination of medical marker and instrument is implemented prior to every use or at the start of using the combination in a piece of medical equipment. Consequently, deformations in the detachable or non-detachable connection between medical marker and instrument (which occurred during storage, for example) advantageously do not lead to errors in the navigation of the medical instrument and an incorrect navigation of the medical instrument is advantageously avoided.

A further aspect of the present disclosure relates to a medical navigation system comprising at least one imaging sensor. The at least one imaging sensor is preferably the image sensor of a camera, an x-ray sensor of a computed tomography device or a sensor of a laser scanner.

The system according to the invention further comprises at least one further imaging sensor. Preferably, the system according to the invention has a plurality of imaging sensors, for example image sensors of a first camera and of a second camera. As an alternative or in addition, the system according to the invention comprises a known kinematic system for changing the pose of the imaging sensor and/or of the medical marker in a defined manner. The known kinematic system is preferably the robotic system of a surgical microscope. The known kinematic system is preferably designed to rotate the imaging sensor and/or the medical marker in a defined manner about the x-axis, the y-axis and the z-axis and to displace these in translational fashion along the x-axis, the y-axis and the z-axis. Preferably, the system according to the invention comprises at least one further imaging sensor and a known kinematic system for changing the pose of the medical marker in a defined manner, the medical marker for example being fastened to a medical instrument.

The system according to the invention further comprises a medical marker. By way of example, the medical marker has a geometry as depicted in FIG. 5. Preferably, the medical marker has a plurality of marker elements of predetermined size, shape and relative pose. The medical marker preferably further comprises a fastening means for establishing a detachable connection to a medical instrument. The marker overall, or at least the marker elements, is/are able to be captured by means of the at least one imaging sensor. Capturing an image representation of the marker renders the pose of the latter determinable. The medical marker overall, or at least the marker elements, preferably is/are (an) active marker (elements) designed to emit electromagnetic radiation in the infrared, visible and/or ultraviolet spectrum. Likewise preferably, the medical marker overall, or at least the marker elements, is/are (a) passive marker (elements) designed to reflect electromagnetic radiation in the infrared, visible and/or ultraviolet spectrum.

The system according to the invention further comprises a control unit connected to the imaging sensor and the further imaging sensor and/or the known kinematic system (respectively where present). The system according to the invention further comprises a storage unit connected to the control unit. In this case, the storage unit comprises commands which, upon execution by the control unit, prompt the control unit to carry out the method according to the invention as described above. Expressed differently, the commands are such that the execution thereof prompts the control unit to drive the imaging sensor to capture a first image representation of the medical marker in a first perspective; to drive the at least one further imaging sensor, the known kinematic system and/or the imaging sensor to capture a second image representation of the medical marker in a second perspective, to determine a three-dimensional representation of the medical marker on the basis of the first image representation and the second image representation, to drive the at least one further imaging sensor, the known kinematic system and/or the imaging sensor to capture a third image representation of the medical marker; and to determine a spatial pose of the medical marker on the basis of a comparison of the third image representation and the three-dimensional representation of the medical marker. The storage unit further preferably comprises commands, the execution of which by the control unit prompts the latter to carry out the preferred implementations of the method according to the invention.

The functionalities of the control unit according to the invention can be implemented by electrical or electronic devices or components (hardware), by firmware (ASIC) and/or can be realized by carrying out a suitable program (software). Preferably, the functionalities of the control unit according to the invention are realized or implemented by a combination of hardware, firmware and/or software. By way of example, individual components of the control unit according to the invention for carrying out individual functionalities are in the form of a separately integrated circuit or are arranged on a common integrated circuit.

The individual functionalities of the control unit according to the invention are further preferably in the form of one or more processes which run on one or more processors in one or more electronic computers and which are generated when carrying out one or more computer programs. In this case, the control unit is designed to cooperate with the other components, in particular the imaging sensor, the at least one further imaging sensor and/or the known kinematic system, in order to implement the functionalities of the system according to the invention as described herein. It is further evident to a person skilled in the art that the functionalities of a plurality of computers (data-processing equipment, control units, controllers) can be combined or can be combined in a single piece of equipment, or that the functionality of one certain piece of data-processing equipment may be available distributed over a multiplicity of pieces of equipment in order to realize the functionalities of the control unit according to the invention.

In a particularly preferred embodiment of the system according to the invention, the latter is integrated in a surgical microscope. In this case, the surgical microscope preferably comprises an imaging sensor and at least one further imaging sensor and/or a known kinematic system, with the known kinematic system being designed for the defined rotation (x, y, z) and translation (x, y, z) of a medical instrument and/or at least one of the imaging sensors. According to this embodiment, the reference coordinate system is preferably the coordinate system of the surgical microscope. Further preferably, the imaging sensor is the image sensor of a main observer camera of the surgical microscope. Particularly preferably, a further imaging sensor is the image sensor of a surround camera. Likewise preferably, the known kinematic system is a robotic system of the surgical microscope for guiding a medical instrument, in particular a surgical instrument. The control unit of the surgical microscope is preferably designed as control unit of the system according to the invention and, in particular, designed to carry out the method according to the invention, as described above, on the basis of commands stored on a storage unit of the surgical microscope.

Within the scope of the present disclosure, a surgical microscope is understood in the broadest sense to be a microscope suitable for use during an operation. The surgical microscope preferably has a mount which allows imaging of the operating region independently of head movements of the surgeon. Further preferably, the surgical microscope comprises at least one beam splitter and at least two eyepieces. Likewise preferably, the surgical microscope comprises at least one imaging sensor. Further preferably, the surgical microscope comprises a main observer camera and a surround camera. The surgical microscope may comprise kinematic or robotic aids for carrying out surgical interventions. As an alternative, a surgical microscope may be denoted a medical engineering microscope, a medically approved microscope or a medical microscope.

A further aspect of the present disclosure relates to a computer program comprising commands which, when executed by a control unit as described above, preferably of a surgical microscope or system as described above, cause the surgical microscope or system as described above to carry out the method according to the invention as described above. The computer program preferably comprises commands which, when executed by a control unit as described above, preferably of a surgical microscope or system as described above, cause the surgical microscope or system as described above to carry out the method according to the invention, in accordance with one of the preferred implementations, as described above. In this case, the computer program according to the invention is preferably stored in a volatile memory, for example a RAM element, or in a non-volatile storage medium, for example a CD-ROM, a flash memory or the like.

A further aspect of the present disclosure relates to the use of a three-dimensional representation of a medical marker for registering a medical instrument, a patient and/or a piece of medical equipment, wherein the three-dimensional representation is determined on the basis of a first image representation captured in a first perspective and a second image representation captured in a second perspective, the image representations being of the medical marker, and wherein the registration comprises capturing a third image representation of the medical marker and determining a spatial pose of the medical marker on the basis of a comparison of the third image representation and the three-dimensional representation of the medical marker. Preferred developments of the use according to the invention correspond to the above-described preferred implementations of the method according to the invention.

Further preferred embodiments of the invention will become clear from the other features set out in the dependent claims. The various embodiments of the invention that are set forth in this application can advantageously be combined with one another, unless specifically stated otherwise.

DESCRIPTION OF THE FIGURES

The invention is explained below in illustrative embodiments and with reference to the attached drawings, in which:

FIG. 1 shows a schematic representation of a system 50 according to the invention in one embodiment, the system 50 being part of a surgical microscope 10.

Figure 1:
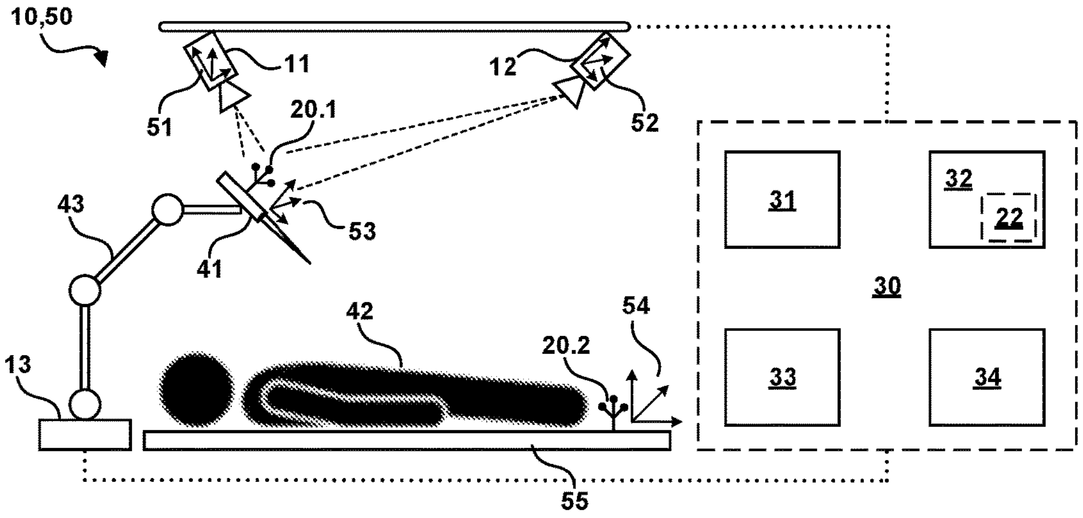
FIG. 1 shows a schematic representation of a system according to the invention in one embodiment.

The surgical microscope 10 comprises a patient couch 55 with a patient 42 disposed thereon. The patient couch 55 and/or the patient 42 define a coordinate system of the patient 54, which forms a reference coordinate system. A medical marker 20.2 is arranged on the patient couch for the purposes of registering the coordinate system 54. In this case, a coordinate system of the marker 20.2 corresponds to the coordinate system 54. The surgical microscope 10 further comprises a piece of medical equipment 43 for holding and guiding a medical instrument 41 by means of a known kinematic system 13. By way of example, the medical instrument is a pointer, an awl, a scalpel, a probe or the like.

A further medical marker 20.1 is arranged on the medical instrument 41. An alignment of the marker 20.1 defines a coordinate system 53 with respect to the medical marker 20.1 and/or with respect to the medical instrument 41. Each of the medical markers 20.1 and 20.2 comprises three marker elements 21, which are able to be captured by means of an imaging sensor and which have a predetermined geometry (in particular size and shape) and relative spatial pose. Even though the medical markers 20.1 and 20.2 were produced according to identical specifications in relation to their geometry, the geometry of the medical markers 20.1 and 20.2 differs on account of production-related variations.

The surgical microscope 10 further preferably comprises a first camera 11 and a second camera 12. The first camera 11 is intrinsically and extrinsically calibrated and a coordinate system 51 of the first camera 11 is able to be mapped or transformed into the reference coordinate system 54 by means of a first parameter set of a rigid body transformation. The second camera 12 is likewise intrinsically and extrinsically calibrated and a coordinate system 52 of the second camera 12 is able to be mapped or transformed into the reference coordinate system 54 by means of a second parameter set of a rigid body transformation. The coordinate system 51 of the first camera 11 is consequently able to be mapped or transformed into the coordinate system 52 of the second camera by means of a third parameter set of a rigid body transformation. The first camera 11 and the second camera 12 have a stationary embodiment. Should the cameras 11, 12 be pivotable, the parameter sets thereof are adjusted accordingly.

The surgical microscope 10 further comprises a control apparatus 30 which is connected for data and signal transmission purposes to the first camera 11, the second camera 12 and the known kinematic system 13, in order to transmit signals to and receive signals from these. The control apparatus 30 comprises a control unit 31, a storage unit 32, a display 33 and a user interface 34 for receiving user inputs.

Commands which are carried out when a user selects a corresponding program by way of the user interface 34 are stored in the storage unit 32. These commands cause the control unit 31 to drive the first camera 11 to capture a first image representation of the marker 20.1 from the perspective of the first camera 11 and to drive the second camera 12 to capture a second image representation of the marker 20.1 from the perspective of the second camera 12.

Further, a three-dimensional representation 23 of the markers 20 in accordance with the specified geometry of the same is stored in the storage unit 32. On the basis of the image representations of the marker 20.1 captured by means of the first camera 11 and the second camera 12, the control unit 31 adjusts the three-dimensional representation 23 of the marker 20.1 by means of a photometric method. In particular, the control unit 31 transforms the first image representation into the coordinate system 52 of the second camera 12 by means of the first parameter set and determines a deviation from the second image representation there. Likewise, the control unit 31 transforms the second image representation into the coordinate system 51 of the first camera 11 by means of the second parameter set and determines a deviation from the first image representation there. The control unit 31 then varies the image representations by calculation such that the determined deviations are minimized. On the basis of image representations determined in this way, in the case of which the deviations are minimal, the control unit 31 finally determines an adjusted three-dimensional representation 23 of the marker 20.1 and stores the said three-dimensional representation in the storage unit 32. In principle, the aforementioned steps are likewise performable for the medical marker 20.2, with two image representations thereof being captured by the first camera 11 and the second camera 12. In this case, an adjusted three-dimensional representation 23 of the marker 20.2 would be created and stored.

Subsequently, the control unit 31 drives the first camera 11 to capture a third image representation of the medical marker 20.1. Using the third image representation of the marker 20.1 and the determined adjusted representation 23 of the marker 20.1, the control unit 31 determines a spatial pose of the marker 20.1 with improved accuracy. This spatial pose is able to be mapped or transformed into the coordinate system 54 of the patient 42 on the basis of the first parameter set. Consequently, the medical instrument 41 can be navigated in the coordinate system 54 of the patient 42 with improved accuracy by means of the known kinematic system 13 of the piece of medical equipment 43. Further, a current position of the medical instrument 41 can be displayed on the display 33, overlaid on presurgical image data registered in the coordinate system 54 of the patient 42, in order to assist the work of a surgeon.

Figure 2:
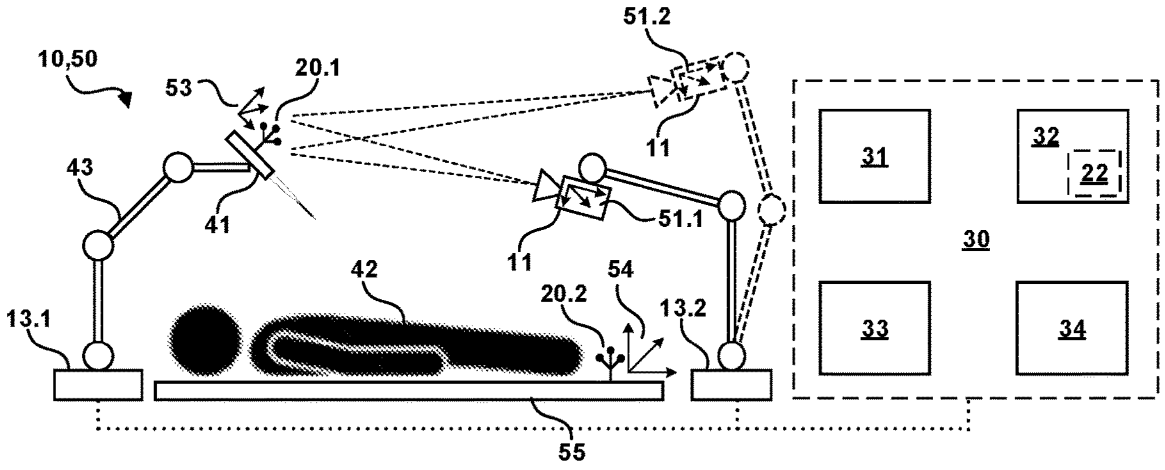
FIG. 2 shows a schematic representation of a system according to the invention in a further embodiment.

FIG. 2 shows a schematic representation of a system 50 according to the invention in a further embodiment, the system being part of a surgical microscope 10. Inasmuch as the system 50 corresponds to the system 50 described with reference to FIG. 1, there is no repeated description of the identical components below. Instead, only differences in the embodiments are discussed in detail.

In contrast to the above-described embodiment in FIG. 1, the surgical microscope 10 in FIG. 2 has only one camera 11. However, the latter is arranged on a second known kinematic system 13.2 and is displaceable and rotatable in three spatial directions by way of said kinematic system. The surgical microscope 10 further comprises a first known kinematic system 13.1, which corresponds to the kinematic system 13 explained with reference to FIG. 1. The second known kinematic system 13.2 is designed to move the camera 11, as a result of which a coordinate system 51 of the camera 11 is translated and rotated relative to a coordinate system 54 of the patient 42. Using the calibration of the kinematic system 13.2, it is possible to derive corresponding parameter sets of a rigid body rotation in order to map or transform the coordinate system 51 of the camera 11 into the coordinate system 54 of the patient 42 in every one of the positions and in order to map or transform the coordinate system 51.1 of a first position of the camera 11 into the coordinate system 51.2 of a second position of the camera 11.

The surgical microscope 10 further comprises a control apparatus 30 which is connected for data and signal transmission purposes to the camera 11, the first known kinematic system 13.1 and the second known kinematic system 13.2, in order to transmit signals to and receive signals from these. Commands which are carried out when a user selects a corresponding program by way of the user interface 34 are stored in the storage unit 32. These commands cause the control unit 31 to move the camera 11 into a first position in order to capture a first image representation of the marker 20.1 by means of the second known kinematic system 13.2 and to move the said camera into a second position which differs from the first position in order to capture a second image representation of the marker 20.1 by means of the second known kinematic system 13.2. On the basis of the image representations of the marker 20.1 captured by means of the camera 11 in the two positions of the second known kinematic system 13.2, the control unit 31 adjusts the three-dimensional representation 23 of the marker 20.1 by means of a photometric method. In particular, the control unit 31 transforms the first image representation of the marker into the coordinate system 51.2 at the second position of the known kinematic system 13.2 and determines a deviation from the second image representation of the marker 20.1 there. Further, the control unit 31 transforms the second image representation of the marker into the coordinate system 51.1 at the first position of the known kinematic system 13.2 and determines a deviation from the first image representation of the marker 20.1 there. The control unit 31 then varies the image representations by calculation such that the determined deviations are minimized. On the basis of the image representations determined in this way, in the case of which the deviations are minimal, the control unit 31 finally determines an adjusted three-dimensional representation 23 of the marker 20.1 and stores the said three-dimensional representation in the storage unit 32. In principle, the aforementioned steps are likewise performable for the medical marker 20.2, with an image representation thereof being captured in each of the two positions of the first camera 11. In this case, an adjusted three-dimensional representation 23 of the marker 20.2 would be created and stored.

Subsequently, the control unit 31 drives the first camera 11 to capture a third image representation of the medical marker 20.1. Using the third image representation of the marker 20.1 and the determined adjusted representation 23 of the marker 20.1, the control unit 31 determines a spatial pose of the marker 20.1 with improved accuracy. This spatial pose is able to be mapped or transformed into the coordinate system 54 of the patient 42 on the basis of the first parameter set. Consequently, the medical instrument 41 can be navigated in the coordinate system 54 of the patient 42 with improved accuracy by means of the known kinematic system 13 of the piece of medical equipment 43. Further, a current position of the medical instrument 41 can be displayed on the display 33, overlaid on presurgical image data registered in the coordinate system 54 of the patient 42, in order to assist the work of a surgeon.

Figure 3:
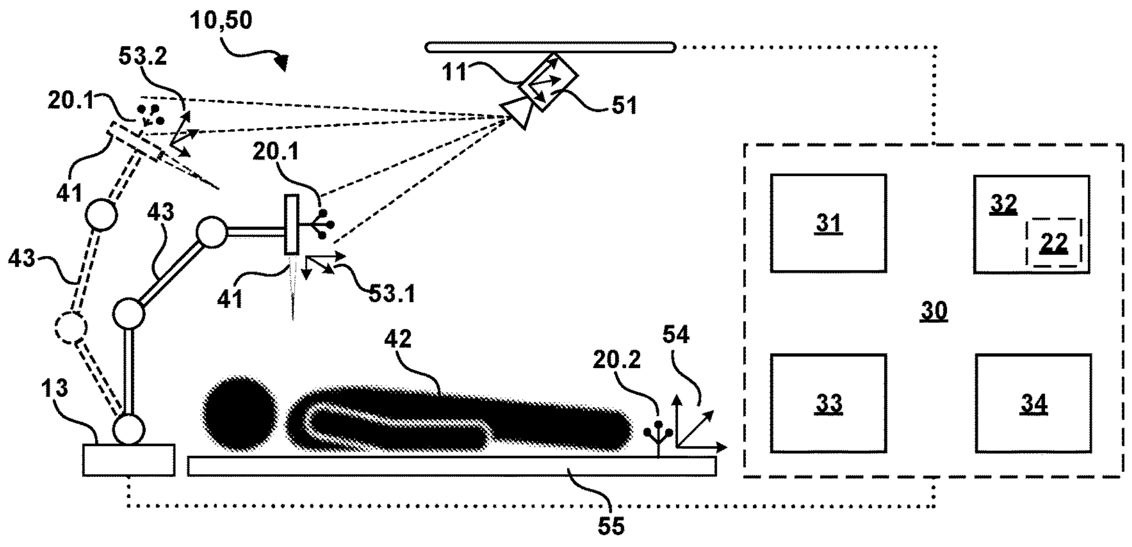
FIG. 3 shows a schematic representation of a system according to the invention in a further embodiment.

FIG. 3 shows a schematic representation of a system 50 according to the invention in a further embodiment, the system being part of a surgical microscope 10. Inasmuch as the system 50 corresponds to the system 50 described with reference to FIG. 1 or 2, there is no repeated description of the same components below. Instead, the differences in the embodiments are discussed in detail.

In contrast to the above-described embodiment in FIG. 1, the surgical microscope 10 in FIG. 3 has only one stationary camera 11. The surgical microscope 10 further comprises a control apparatus 30 which is connected for data and signal transmission purposes to the camera 11 and the known kinematic system 13, in order to transmit signals to and receive signals from these. Commands which are carried out when a user selects a corresponding program by way of the user interface 34 are stored in the storage unit 32. These commands cause the control unit 31 to move the marker 20.1 into a first position by means of the known kinematic system 13 in order to capture a first image representation and to move the marker 20.1 into a second position by means of the known kinematic system 13 in order to capture a second image representation.

On the basis of the image representations of the marker 20.1 captured by means of the camera 11 in the two positions of the known kinematic system 13, the control unit 31 adjusts the three-dimensional representation 23 of the marker 20.1 by means of a photometric method. In particular, the control unit 31 transforms the first image representation of the marker 20.1 into the coordinate system 53.2 at the second position of the known kinematic system 13 and determines a deviation from the second image representation of the marker 20.1 there. Further, the control unit 31 transforms the second image representation of the marker 20.1 into the coordinate system 53.1 at the first position of the known kinematic system 13 and determines a deviation from the first image representation of the marker 20.1 there. The control unit 31 then varies the image representations by calculation such that the determined deviations are minimized. On the basis of the image representations determined in this way, in the case of which the deviations are minimal, the control unit 31 finally determines an adjusted three-dimensional representation 23 of the marker 20.1 and stores the said three-dimensional representation in the storage unit 32. The aforementioned steps are not performable for improving the 3-D representation of the medical marker 20.2.

Subsequently, the control unit 31 drives the first camera 11 to capture a third image representation of the medical marker 20.1. Using the third image representation of the marker 20.1 and the determined adjusted representation 23 of the marker 20.1, the control unit 31 determines a spatial pose of the marker 20.1 with improved accuracy. This spatial pose is able to be mapped or transformed into the coordinate system 54 of the patient 42 on the basis of the first parameter set. Consequently, the medical instrument 41 can be navigated in the coordinate system 54 of the patient 42 with improved accuracy by means of the known kinematic system 13 of the piece of medical equipment 43. Further, a current position of the medical instrument 41 can be displayed on the display 33, overlaid on presurgical image data registered in the coordinate system 54 of the patient 42, in order to assist the work of a surgeon.

Figure 4:
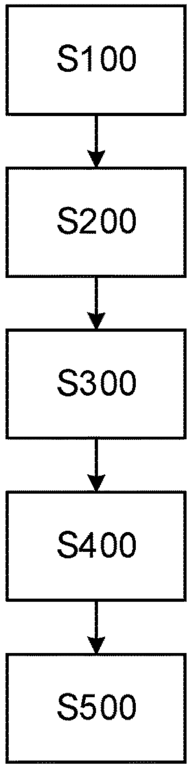
FIG. 4 shows a schematic flowchart of a method according to the invention in one implementation.

FIG. 4 shows a schematic flowchart of a method of medical navigation according to the invention in one implementation. In a first step S100 of the method according to the invention, a first image representation of a medical marker is captured in a first perspective. In a second step S200 of the method according to the invention, a second image representation of the medical marker is captured in a second perspective. In a third step S300 of the method according to the invention, a three-dimensional representation of the medical marker is determined on the basis of the first image representation and the second image representation. In a fourth step S400 of the method according to the invention, a third image representation of the medical marker is captured. In a fifth step S500 of the method according to the invention, a spatial pose of the medical marker is determined on the basis of the third image representation and the three-dimensional representation of the medical marker.

Figure 5:
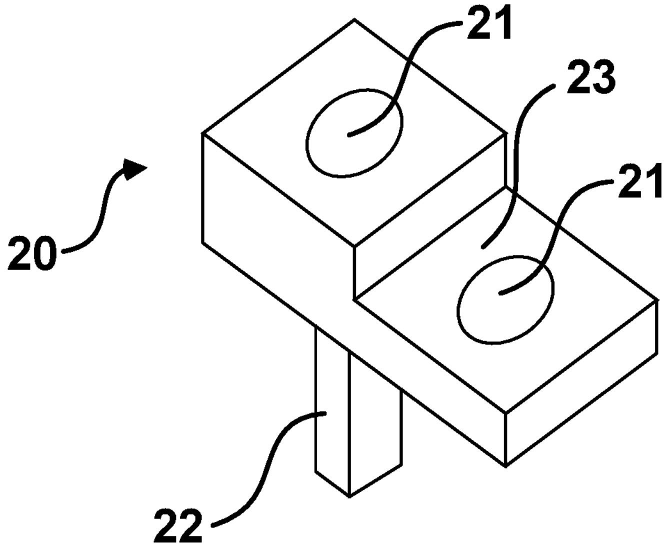
FIG. 5 shows a schematic representation of a marker for use in the method according to the invention and in the system according to the invention.

FIG. 5 shows a schematic representation of a marker 20 for use in the method according to the invention and in the system 50 according to the invention. The depicted marker 20 has two circular marker elements 21, which are arranged in two different planes. Each of the marker elements 21 is able to be captured using a camera and has a different colour from the colour of the other marker element 21 for unique recognizability. The marker 20 further comprises a fastening clip 22 as a fastening means, for fastening it to a medical instrument 41. A marker for use in the method according to the invention and in the system 50 according to the invention preferably has more than two, for example three, four or more marker elements that have a fixed (known) relative arrangement and are uniquely identifiable. The marker elements may be printed on the surface or may be raised and may be planar or arranged on different planes.

LIST OF REFERENCE SIGNS

10 Surgical microscope
11 First camera
12 Second camera
13 Known kinematic system
20 Medical marker
21 Marker elements
22 Fastening clip
23 Three-dimensional representation
30 Control apparatus
31 Control unit (CPU)
32 Storage unit
33 Display
34 User interface
41 Medical instrument
42 Patient
43 Piece of medical equipment
50 System
51 Coordinate system of the first camera
52 Coordinate system of the second camera
53 Coordinate system of the marker/medical instrument
54 Coordinate system of the patient
55 Patient couch
S100 Capturing a first image representation
S200 Capturing a second image representation
S300 Determining a three-dimensional representation
S400 Capturing a third image representation
S500 Determining a spatial pose

The invention claimed is:

1. A method of medical navigation comprising:

capturing a first image representation of a medical marker in a first perspective;

capturing a second image representation of the medical marker in a second perspective;

determining a three-dimensional representation of the medical marker based on the first image representation and the second image representation, the three-dimensional representation including a three-dimensional volume of the medical marker;

capturing a third image representation of the medical marker; and determining a spatial pose of the medical marker based on a comparison of the third image representation and the three-dimensional representation of the medical marker.

2. The method according to claim 1, wherein the first image representation, the second image representation and/or the third image representation are determined by means of at least one imaging method.

3. The method according to claim 1, wherein the medical marker has a geometry and the three-dimensional representation of the medical marker is determined on the basis of the first image representation, the second image representation and information relating to the geometry of the marker.

4. The method according to claim 1, wherein a relationship between a coordinate system of the first image representation and a coordinate system of the second image representation is determined by a parameter set of a rigid body transformation.

5. The method according to claim 4, wherein determining the three-dimensional representation of the medical marker further comprises at least one of:

(i) transforming the first image representation of the marker into the coordinate system of the second image representation using the parameter set, and determining a first deviation between the transformed first image representation of the marker and the second image representation of the marker; and ii) transforming the second image representation of the marker into the coordinate system of the first image representation using the parameter set, and determining a second deviation between the transformed second image representation of the marker and the first image representation of the marker; and determining the three-dimensional representation of the medical marker on the basis of at least one of the first deviation and the second deviation.

6. The method according to claim 5, wherein the determination of the three- dimensional representation of the marker comprises adjustment of information relating to the geometry of the marker on the basis of at least one of the first deviation and the second deviation.

7. The method according to claim 1, wherein the first image representation is captured by a first camera and the second image representation is captured by a second camera.

8. The method according to claim 7, wherein a relationship between a coordinate system of the first camera and a coordinate system of the first image representation is defined by first intrinsic parameters of the first camera, and a relationship between a coordinate system of the second camera and the coordinate system of the second image representation is defined by second intrinsic parameters of the second camera.

9. The method according to claim 1, wherein the first image representation is captured in a first position of a camera and the second image representation is captured in a second position of the camera; or the first image representation of a first pose of the marker is captured by a camera and the second image representation of a second pose of the marker is captured by the camera.

10. The method according to claim 1, wherein the medical marker is fastened to a medical instrument, the third image representation is a combination of the medical marker and the medical instrument.

11. The method according to claim 10, wherein further the first image representation and the second image representation of the combination of medical marker and medical instrument are captured and the three-dimensional representation of the combination of the medical marker and the medical instrument is determined on the basis of the first image representation and the second image representation and the spatial pose of the combination of medical marker and medical instrument is determined.

12. A medical navigation system comprising:

at least one imaging sensor;

a medical marker;

at least one further imaging sensor and/or a known kinematic system for changing the pose of the imaging sensor and/or the medical marker in a defined manner;

a control unit connected to the imaging sensor and the further imaging sensor and/or the known kinematic system;

a storage unit connected to the control unit and comprising commands which, upon execution by the control unit, cause the latter to carry out the method according to claim 1.

13. The system according to claim 12, integrated in a surgical microscope.

14. A non-transitory computer-readable storage medium storing a computer program comprising commands which, upon execution by a control unit, cause the control unit to carry out the method according to claim 1.

15. A method of using a three-dimensional representation of a medical marker for registering a medical instrument, a patient and/or a piece of medical equipment, the method comprising:

determining the three-dimensional representation of the medical marker based on a first image representation captured in a first perspective and a second image representation captured in a second perspective, the image representations being of the medical marker, and determining a spatial pose of the medical marker based on comparing a third image representation of the medical marker and the three-dimensional representation of the medical marker, the three-dimensional representation including a three-dimensional volume of the medical marker.

16. The method according to claim 1, wherein the three-dimensional representation of the medical marker denotes a three-dimensional model of a shape or a geometry of the medical marker.

* * * * *